United States Patent
Aoyagi

(10) Patent No.: US 6,555,053 B1
(45) Date of Patent: Apr. 29, 2003

(54) METHOD FOR SUPPLYING STERILIZATION/DEODORIZATION GAS AND APPARATUS THEREFOR

(75) Inventor: Kohei Aoyagi, Tokyo (JP)

(73) Assignee: Kabushiki Kaisha Sunseal, Osaka (JP)

( * ) Notice: Subject to any disclaimer, the term of this patent is extended or adjusted under 35 U.S.C. 154(b) by 0 days.

(21) Appl. No.: 09/460,867

(22) Filed: Dec. 14, 1999

(30) Foreign Application Priority Data

Jan. 12, 1999 (JP) .............................. 11-005566

(51) Int. Cl.[7] .............................. A61L 2/00; A61L 9/00; A62B 7/08; B01J 19/08; C01B 7/00
(52) U.S. Cl. .............................. 422/5; 422/22; 422/49; 422/120; 422/186.3; 422/186.12; 422/306; 204/157.1 R; 204/157.44; 204/157.48; 204/903; 204/904
(58) Field of Search ..................... 422/1, 5, 22, 49, 422/120–125, 186, 292, 37, 295, 300, 305–307, 186.3, 186.12; 204/157.44, 904, 157.48, 903, 157.1 R

(56) References Cited

U.S. PATENT DOCUMENTS

| | | | |
|---|---|---|---|
| 4,414,180 A | * 11/1983 | Fisher | 422/186 |
| 4,456,511 A | * 6/1984 | Fisher | 204/157.1 R |
| 4,829,129 A | * 5/1989 | Kelley | |
| 4,874,489 A | * 10/1989 | Callerame | 204/157.44 |
| 5,141,722 A | * 8/1992 | Nagashima | 422/292 |
| 5,422,068 A | * 6/1995 | Shalaby et al. | 422/22 |
| 5,695,814 A | * 12/1997 | Wellinghoff et al. | |
| 5,713,137 A | * 2/1998 | Fujita | |

OTHER PUBLICATIONS

Derwent 2001–483695.*

* cited by examiner

Primary Examiner—Robert J. Warden, Sr.
Assistant Examiner—Monzer R. Chorbaji
(74) Attorney, Agent, or Firm—Dennis G. LaPointe; Mason Law, P.A.

(57) ABSTRACT

According to the present invention, provided are a method whereby a sterilization/deodorization gas is supplied by irradiating a stabilized chlorine dioxide gel or liquid with ultraviolet radiation, and a sterilization/deodorization gas supply apparatus which comprises: a chemical container used to hold a chemical gel or liquid which is used for sterilization and deodorization, and as an insecticide or an insectifuge; an ultraviolet radiation unit for projecting ultraviolet radiation onto the chemical and for generating a dispersed gas; and a gas discharge unit for extracting from the chemical container gas elements that are to be dispersed by the ultraviolet radiation unit. With this arrangement, a chlorine dioxide gas that can effectively perform sterilization and deodorization can be easily and safely stored, handled and supplemented by employing the chemical reactive propagative effects of ultraviolet radiation.

14 Claims, 1 Drawing Sheet

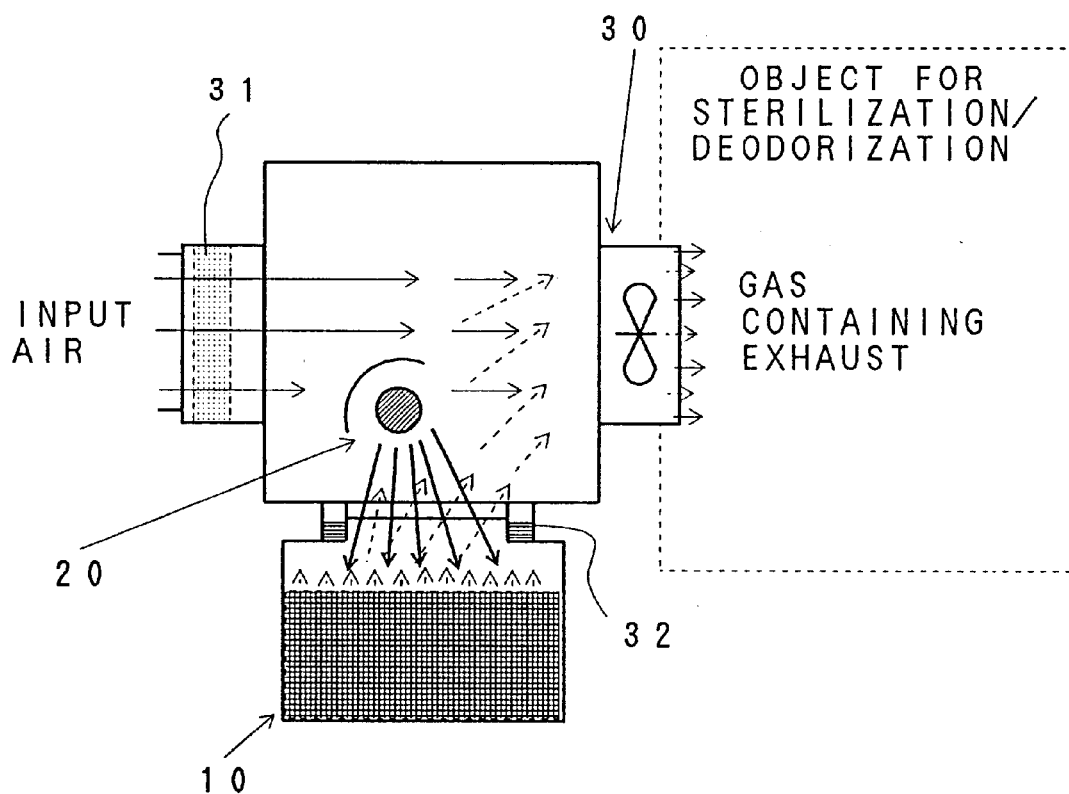
F I G. 1

METHOD FOR SUPPLYING STERILIZATION/DEODORIZATION GAS AND APPARATUS THEREFOR

BACKGROUND OF THE INVENTION

1. Field of the Invention

The present invention relates to a sterilization/deodorization gas supply method, and an apparatus therefor, for easily and safely supplying as gas, liquid or gel chemicals which are used for sterilization or deodorization or as an insecticide.

2. Related Arts

Various types of bactericides, deodorants and insecticides are in use today. When these chemicals are administered for sterilization or deodorization, or as an insecticide, a sprayer or an atomizer is employed to dispense them undiluted, or as dilute solutions or powders.

When such chemicals are administered in this fashion, the sprayer or the atomizer which is used must be filled specially, and a certain amount of physical labor is required to load the device. Therefore, when a dispensing device is being filled with a chemical, the possibility exists that the person performing the work may be injured, especially if the chemical is one for which use is limited because of its residual toxicity. For this and other reasons, there is a demand for a method and an apparatus with which sterilization/deodorization and the application of an insecticide can be safely and easily performed.

For sterilization or deodorization, there are in addition a number of chemical compounds which can be used; for example, chemical compounds containing aromatic substances which neutralize bad odors, or chemical compounds containing adsorbents, such as active carbon, activated clay and silica gel, which absorb or neutralize bad odors. However, since such adsorbents or neutralizers have expiration periods, the effects provided by these chemical compounds gradually decline. In addition, the chemical compounds can not be relied on to provide precise sterilization effects.

Therefore, a method which involves the evaporation of a stabilized chlorine dioxide ($ClO_2$) solution is widely employed at medical facilities for bedding, clothing, patient rooms, and ambulances. It is also well known that stabilized chlorine dioxide has a bleaching function, and for this reason it is employed in many manufacturing processes. However, since high density chlorine dioxide of industrial strength is a strong oxidizer, when it is used it may react with other materials and generate a high concentration of life threatening chlorine gas. And since with chlorine dioxide there is also the danger of explosion, a 5% solution of stabilized chlorine dioxide, such as is produced by International Dioxide Inc., is provided as a less dangerous and easier to handle chlorine dioxide solution, which when employed is diluted as needed for the application.

While a chlorine dioxide gas obtained by the vaporization of a stabilized chlorine dioxide solution does not have a sharp and pungent odor and is safe to handle, when applied to objects it is a very effective agent for sterilization, deodorization and disinfection. Superior effects, achieved over a short period of time, can be obtained with chlorine dioxide gas when it is used to destroy or prevent the growth of various types of bacteria, mold and other disease-carrying microorganisms. Further, its deodorization capabilities are also pronounced, and odors, especially those produced by chemical materials and by putrefaction, which accompanies the propagation of microorganisms, can be prevented.

Since the stabilized chlorine dioxide which has the above superior characteristics is normally provided as an aqueous solution, the delivery, the handling and the resupply of this solution must be performed very carefully, and the apparatus which is used for the vaporization process is complicated. While the stabilized chlorine dioxide solution may be employed as a powder or as particles, by using zeolite, a porous material, to absorb it, these forms are not appropriate when chlorine dioxide is stably discharged for an extended period of time. Further, since an alkali generator must also be used as an activator, the use of chlorine dioxide is limited.

To resolve the above shortcomings, the present applicant proposed an apparatus wherein to produce a gas which is to be dispersed, heat is applied to a gelled chemicals which can be handled safely (Japanese Patent Application No. Hei 10-76467). However, the apparatus employed to supply the needed heat consumes a great deal of power, and therefore, depending on the application, there may be a demand for an apparatus that does not employ a heater.

SUMMARY OF THE INVENTION

The present invention is provided to resolve the above shortcomings, especially by focusing on a chlorine dioxide gas that can effectively perform the sterilization and deodorization functions. It is, therefore, one objective of the present invention to provide a sterilization/deodorization gas supply method whereby the chemical reactive, propagative effects of ultraviolet radiation are employed to easily and safely store, handle and supplement the supply of a sterilization/deodorization gas, and an apparatus therefor.

To achieve the above objective, according to the present invention, provided is a method whereby a sterilization/deodorization gas is supplied by irradiating a stabilized chlorine dioxide gel or liquid with ultraviolet radiation. In this invention, the stabilized chlorine dioxide gel or liquid which is to be exposed to ultraviolet radiation is generally.stored in a chemical container. The ultraviolet radiation may also be projected onto zeolite, for example, a porous material which has absorbed or been impregnated with a stabilized chlorine dioxide solution.

Further, according to the present invention, as is shown in FIG. 1 a sterilization/deodorization gas supply apparatus comprises:

- a chemical container 10 used to retain a chemical gel or liquid that functions as a sterilizer, an insecticide, an insectifuge or a deodorant;
- ultraviolet radiation means 20 for projecting ultraviolet radiation onto the chemical gel or liquid in the chemical container 10; and
- a gas discharge unit 30 for extracting from the chemical container 10 gas elements, produced by the ultraviolet radiation means 20, which are to be dispersed.

Generally, the chemical is a stabilized chlorine dioxide gel or liquid. Since the chlorine dioxide gas, which is supplied performs sterilization and deodorization effectively, the objective of the present invention can be achieved. In the following explanation, therefore, stabilized chlorine dioxide is employed as the chemical according to the present invention, and the stabilized chlorine dioxide container 10 is employed as the chemical container.

The irradiation source provided for the ultraviolet radiation means 20 can be a fluorescent chemical lamp wherein, instead of a fluorescent material for visible light, a fluorescent material is provided on the inner wall of a mercuryvapor discharge tube, which has the same structure as that of a fluorescent lamp used for illumination and which generates a large amount of ultraviolet elements.

In addition, according to the present invention, when the amount of ultraviolet radiation produced by the ultraviolet radiation means 20 is adjusted as needed, the chemical reactive, propagative effects of the ultraviolet radiation can be adjusted and the amount of gas which is dispersed can be controlled. The amount of ultraviolet radiation can also be adjusted by controlling the discharge of an ultraviolet radiation lamp, or by providing a filter or a partial shutter along a radiation route.

According to the present invention, the sterilization/deodorization gas can be easily and safely supplied, and the apparatus which is employed for this purpose is very simple and safe. Further, since instead of a mist a stabilized chlorine dioxide gas of an adequate density is obtained by vaporizing a chlorine dioxide gel or liquid and is projected onto an object to be sterilized and deodorized, the gas can fully permeate the object, and its sterilization and deodorization effects can be clearly demonstrated. And as a result, since no residual chlorine dioxide elements are deposited in the object, no corrosion of the object will occur.

The sterilization/deodorization gas discharged by the gas supply method and apparatus of the present invention is released through a bag or a box made of an air-tight material, or a plastic cover, or projected directly onto medical waste, bedding, mattresses, clothing and footwear. In addition, the sterilization/deodorization gas can be released into a specific space, such as a food producing/processing facility, represented here by a flour mill, a ward or the interior of an ambulance. Furthermore, to prevent bedsores, the sterilization/deodorization gas of the present invention can be projected onto bedding, such as cloth or air mattresses.

According to the present invention, an ozone generator, which will increase the effectiveness of the sterilization process, can also be provided near the gas discharge port of the gas discharge unit 30. In addition, according to the present invention, provided is a sterilization/deodorization system that comprises absorption means, for absorbing stabilized chlorine dioxide elements in the exhaust of the sterilization/deodorization gas that has been supplied by the apparatus and has passed through an object to be sterilized and deodorized. With this arrangement, no chlorine dioxide elements are discharged externally, and the release of air pollutants is prevented.

BRIEF DESCRIPTION OF THE DRAWING

FIG. 1 is a diagram for explaining the basic structure of a sterilization/deodorization gas supply apparatus according to the present invention.

DETAILED DESCRIPTION OF THE PREFERRED EMBODIMENT

Before a specific explanation is given for a sterilization/deodorization gas supply apparatus according to the present invention, a chemical used for the present invention will be described. For this invention, a variety of chemicals, such as stabilized chlorine dioxide, formalin, cresol, phenol, DDT, parathion and ethanol, which are used for sterilization to destroy disease-carrying microorganisms and as agricultural disinfectants and insecticides, can be employed for sterilization, disinfection, antisepsis, antibacterial use and deodorization, and as insecticides. While all conventional sterilization agents can be employed for this invention, in the following explanation stabilized chlorine dioxide gel or liquid is the chemical which is employed.

An explanation will now be given for stabilized chlorine dioxide when it is used as a primary element. A stabilized chlorine dioxide gel used in this invention can be manufactured by any well known means, such as a method according to which it is mixed with agar or gelatin and a bridging agent to form a gel. As for the chemical properties of chlorine dioxide, it is well known that it reacts strongly with a double linked portion and a benzene nucleus, and also reacts with a cyanide compound, hydrogen sulfide and protein, but does not react with saturated and unsaturated fatty acids. By using this property, a stabilized chlorine dioxide solution can be gelatinized by employing a gelation agent obtained, for example, by mixing gelatin with a saturated fatty acid, such as stearic acid or palmitic acid, or an unsaturated fatty acid, such as oleic acid or linoleic acid.

The speed of evaporation of the stabilized chlorine dioxide gel can be adjusted in accordance with the amount of ethyl alcohol contained in a gelation agent, and the size of the evaporation area in a container. The evaporation speed can also be varied by adjusting the strength of the ultraviolet radiation with which the chlorine dioxide is irradiated and the temperature, both of which greatly affect the vaporization speed. Also, since stabilized chlorine dioxide changes, depending on the pH value, and is most stable at a reading of approximately pH 9, it is preferable that, as needed, an alkali material be added to the chlorine dioxide to maintain a pH 9 reading.

Since the stabilized chlorine dioxide gel is more suitable for storage, transportation and handling than is the aqueous solution, and can be safely employed using a small container, in this invention it is preferable that a cartridge container which is used be filled with a stabilized chlorine dioxide gel, rather than a stabilized chlorine dioxide aqueous solution.

The preferred embodiment of the present invention will now be described while referring to the accompanying drawing. The present invention, however, is not limited to this embodiment.

FIG. 1 is a diagram showing the basic arrangement of a sterilization/deodorization gas supply apparatus according to the present invention. A stabilized chlorine dioxide gel or liquid is contained in a chemical container 10, and ultraviolet radiation means 20 is, for example, a fluorescent chemical lamp. It should be noted that temperature control means, an irradiation volume controller and an operating period control timer (none of them shown) can be provided for the ultraviolet radiation means 20.

An operating current control circuit that employs a thyristor or another semiconductor device, or an ultraviolet transmission filter that is located along an irradiation route is appropriate for use as the ultraviolet radiation volume controller; and an appropriate operating current control circuit is a pulse controller that can vary an effective flux, while maintaining a stable discharge, by employing a predetermined or higher peak voltage value. Further, the amount of ultraviolet irradiation can be adjusted by alternately employing a plurality of filters having different transmission levels.

In accordance with the application, a suction fan can be provided on the side of a gas discharge unit 30, or an extraction fan can be provided to the rear of the chemical container 10 and the ultraviolet radiation means 20. When either or both of the suction and extraction fans are employed, a dispersed gas can be effectively extracted or be projected onto an object. A filter 31 is provided on the air intake side.

As is described above, the chemical container 10 is used to store a stabilized chlorine dioxide gel or liquid that is prepared with the above arrangement. Since stabilized chlorine dioxide is dispersed and exhausted as it is consumed, it must be supplemented as needed as the contents of the chemical container 10 are exhausted. Therefore, it is preferable that the chemical container 10 be designed as a detachable cartridge which can be mounted at a connecting portion 32, part of the gas discharge unit 30. While the size and the shape of the apparatus are not particularly limited, a convenient design is one where the cover side is formed so that it is wider, while taking into account the fact that the area which comes into contact with distributed heated air affects the dispersion efficiency.

In this embodiment, the container 10 is cylindrical, and threads on the cover portion engage threads on the connecting portion 32 at the base of the gas discharge unit 30. Therefore, it is easy to supplement the stabilized chlorine dioxide and to exchange containers 10. The shape of the container 10 can be arbitrarily determined, and not only can threads be employed to couple the container 10 with the gas discharge unit 30, but also hooks can be employed to secure the container 10 to the gas discharge unit 30.

The sterilization/deodorization gas supply apparatus can be used to sterilize or to deodorize objects such as medical instruments, medical waste, bedding, mattresses, clothing and footwear which have been enclosed in bags or boxes made of air-tight materials, or in plastic covers; and can be used to sterilize or deodorize specific internal spaces such as the interiors of toilets, patient rooms and ambulances. The apparatus of the present invention can also be employed to help prevent bedsores by producing a sterilization/deodorization gas having an effective density and projecting it onto such bedding as cloth or air mattresses.

In this case, it is convenient for a timer to be provided which can be set in advance to time the operation of the sterilization/deodorization gas supply apparatus, and to control the operating time in accordance with the type and the size of an object or the volume of an enclosed space, such as the interior of a storage bag or a sickroom.

It is preferable that, when employed for objects placed in storage bags or for the interior of a room, means for absorbing exhausted gas (not shown) be provided in order to completely prevent the deposit in a room of residual gas elements which could adversely affect human beings. Normally the density of the stabilized chlorine dioxide in the exhaust is set so that it remains less than 0.1 ppm, the gas absorption means can include, for example, a ceramic formed member, which is chiefly made from an active carbon or animal bone powders, or paper or non-woven cloth containing such a formed member, or an absorption neutralizer such as an organic acid.

The sterilization/deodorization gas supplying apparatus of this invention can be employed for the destruction of vermin and the sterilization and the deodorization of air mattresses; medical instruments; medical waste; bedding; clothing; wards; ambulances interiors; residential space; stores; offices; food processing facilities; computer rooms; lockers; warehouses; engine rooms and passenger compartments of transportation means, such as trains, buses and airplanes; vinyl plastic hothouses; refrigerators; and clothing dryers. The apparatus of the present invention is also effective when used for products such as footwear, sport goods, wigs and accessories, and stuffed toys that are not easy to wash, and for their storage areas.

It is natural that the sizes and the volumes of the sterilization/deodorization gas supply apparatuses of this invention vary between those for use in large airplanes and warehouses, and those for use in offices, stores and homes. Further, in accordance with the application, an additional apparatus such as an ozone generator, which is an effective deodorization means, can be combined with the apparatus of the present invention.

As is described above, according to the present invention, a sterilization/deodorization gas produced by the gas supplying method and apparatus of the invention is not a mist but has a fully gaseous form in which no water droplets or aqueous vapor are included. Therefore, the gas can spread so that it is evenly distributed across the surface of an object to be sterilized and deodorized. Further, no soiling, corrosion or deterioration of the object occurs.

Since stabilized chlorine dioxide is formed as a gel, a cartridge container that is easy to handle can be employed, and the storage, delivery and exchange of the container are facilitated. Compared with an apparatus for which a stabilized chlorine dioxide aqueous solution is employed, the apparatus that employs the gel is simpler and more economic.

Various modes of carrying out the invention are contemplated as being within the scope of the following claims which point out and distinctly claim the subject matter regarded as the invention.

What is claimed is:

1. A sterilization/deodorization gas supply apparatus comprising:

a cartridge container containing a stabilized chlorine dioxide in an organic gelatinous agent form;

a gas discharge unit;

ultraviolet radiation means for projecting ultraviolet radiation onto the stabilized chlorine dioxide gel in said cartridge container to release the chlorine dioxide in dry, gaseous form;

said ultraviolet radiation means being located within the gas discharge unit and the cartridge container being in an underlying relationship to the ultraviolet radiation means and detachably coupled to the gas discharge unit, the cartridge container being located such that the chlorine dioxide gas produced is dispersable within an air stream of an air channel within the gas discharge unit;

means for directing the chlorine dioxide gas produced and dispersed in the air stream outside the gas discharge unit through a discharge port for sterilization/deodorization purposes.

2. A sterilization/deodorization gas supply apparatus according to claim 1, further comprising:

an ozone generator provided near the gas discharge port of said gas discharge unit for increasing the effectiveness of a sterilization process.

3. A sterilization/deodorization gas supply apparatus according to claim 1 wherein said ultraviolet radiation means further includes at least one of a temperature control means, an irradiation amount controller and an operating period control timer.

4. A sterilization/deodorization gas supply apparatus according to claim 1 wherein said gas discharge unit further includes a fan for extracting gaseous chlorine dioxide from said chemical container.

5. A sterilization/deodorization gas supply apparatus according to claim 1 wherein said gas discharge unit includes an air inlet.

6. A sterilization/deodorization gas supply apparatus according to claim 5 wherein said air inlet further includes a filter.

7. A sterilization/deodorization gas supply apparatus according to claim 1 further comprising a timer forming the operation of the sterilization/deodorization gas supply apparatus.

8. A sterilization/deodorization gas supply apparatus according to claim 1, wherein the stabilized chlorine dioxide gel is formed by mixing gelatin with a fatty acid to gelatinize a stabilized chlorine dioxide.

9. A sterilization/deodorization gas supply system comprising:
- a sterilization/deodorization gas supply apparatus comprising:
  - a cartridge container containing stabilized chlorine dioxide in an organic gelatinous agent form;
  - a gas discharge unit;
  - ultraviolet radiation means for projecting ultraviolet radiation onto the stabilized chlorine dioxide gel in said cartridge container to release the chlorine dioxide in dry, gaseous form;
  - said ultraviolet radiation means being located within the gas discharge unit and the cartridge container being in an underlying relationship to the ultraviolet radiation means and detachably coupled to the gas discharge unit the cartridge container being located such that the chlorine dioxide gas produced is dispersable within an air stream of an air channel within the gas discharge unit; and
  - means for directing the chlorine dioxide gas produced and dispersed in the air stream outside the gas discharge unit through a discharge port for sterilization/deodorization purposes; and
- an absorption means for absorbing stabilized chlorine dioxide gas that has passed through an object to be sterilized and deodorized.

10. A sterilization/deodorization gas supply system according to claim 9, wherein the stabilized chlorine dioxide gel is formed by mixing gelatin with a fatty acid to gelatinize a stabilized chlorine dioxide.

11. A method for generating a sterilization/deodorization gas comprising the step of irradiating gelatinous stabilized chlorine dioxide with ultraviolet radiation to release the chlorine dioxide in dry gaseous form to comprise the sterilization/deodorization gas, the chlorine dioxide gas being generated in a sterilization/deodorizing gas system comprising:
- a sterilization/deodorization gas supply apparatus comprising:
  - a cartridge container containing stabilized chlorine dioxide in an organic gelatinous agent form;
  - a gas discharge unit;
  - ultraviolet radiation means for projecting ultraviolet radiation onto the stabilized chlorine dioxide gel in said cartridge container to release the chlorine dioxide in dry, gaseous form;
  - said ultraviolet radiation means being located within the gas discharge unit and the cartridge container being in an underlying relationship to the ultraviolet radiation means and detachably coupled to the gas discharge unit, the cartridge container being located such that the chlorine dioxide gas produced is dispersable within an air stream of an air channel within the gas discharge unit; and
  - means for directing the chlorine dioxide gas produced and dispersed in the air stream outside the gas discharge unit through a discharge port for sterilization/deodorization purposes.

12. A method according to claim 11 further including the step of absorbing the stabilized chlorine dioxide gas that has passed through an object to be sterilized and deodorized.

13. A method according to claim 11 further including the step of gelatinizing a stabilized chlorine dioxide with a gelation agent.

14. A method according to claim 11, wherein the stabilized chlorine dioxide gel is formed by mixing gelatin with a fatty acid to gelatinize a stabilized chlorine dioxide.

* * * * *